(12) United States Patent
Wood (10) Patent No.: US 10,517,769 B2
(45) Date of Patent: Dec. 31, 2019

(54) CAST PORTAL

(71) Applicant: Christopher Steven Wood, Edenton, NC (US)

(72) Inventor: Christopher Steven Wood, Edenton, NC (US)

(73) Assignee: Christopher Steven Wood, Edenton, NC (US)

( * ) Notice: Subject to any disclaimer, the term of this patent is extended or adjusted under 35 U.S.C. 154(b) by 198 days.

(21) Appl. No.: 15/443,057

(22) Filed: Feb. 27, 2017

(65) Prior Publication Data

US 2018/0243144 A1    Aug. 30, 2018

(51) Int. Cl.
*A61F 13/04* (2006.01)
*A61F 5/05* (2006.01)

(52) U.S. Cl.
CPC .............. *A61F 13/041* (2013.01); *A61F 5/05* (2013.01)

(58) Field of Classification Search
CPC ................................. A61F 13/041; A61F 5/05
See application file for complete search history.

(56) References Cited

U.S. PATENT DOCUMENTS

| | | | | |
|---|---|---|---|---|
| 3,116,731 A * | 1/1964 | Baxter | ................. | A61F 13/046 602/14 |
| 3,307,537 A * | 3/1967 | Simon | ..................... | A61F 13/04 602/14 |
| 3,656,477 A * | 4/1972 | Thomas | ................. | A61F 13/046 602/14 |
| 3,762,406 A * | 10/1973 | Wells | .................... | A61F 13/046 602/14 |
| 3,998,220 A * | 12/1976 | Cleer, Jr. | .............. | A61F 13/046 602/14 |
| 4,535,779 A * | 8/1985 | Ober | .................... | A61B 5/0408 600/384 |
| 5,196,001 A * | 3/1993 | Kao | ....................... | A61J 1/2093 206/438 |
| 6,120,469 A * | 9/2000 | Bruder | ................. | A61F 13/046 602/13 |
| 6,183,452 B1 | 2/2001 | Bodmer et al. | | |

(Continued)

FOREIGN PATENT DOCUMENTS

FR         2 818 888         7/2002
WO    WO 2009/155715        12/2009

*Primary Examiner* — Kristen Matter
(74) *Attorney, Agent, or Firm* — Katten Muchin Rosenman LLP (57) ABSTRACT

Disclosed are systems, methods, and devices related to a cast portal. The cast portal can be for enabling selective access through a medical cast to a body part covered by the medical cast. One illustrative cast portal includes an interior portion that extends through an entire longitudinal length of the cast portal. The illustrative cast portal can also include an outer housing that defines the bounds of the interior portion. The outer housing can include a top end configured to be positioned distal to the body part covered by the medical cast. The outer housing can also include a bottom end configured to be positioned proximate to the body part covered by the medical cast. The illustrative cast portal can also include a protrusion extending radially outwardly from the outer housing and configured to mechanically couple with the medical cast for attaching the device to the medical cast.

15 Claims, 10 Drawing Sheets

(56) References Cited

U.S. PATENT DOCUMENTS

| | | | | |
|---|---|---|---|---|
| 6,503,214 B1 * | 1/2003 | Talish | ................... | A61F 15/02 |
| | | | | 602/9 |
| 6,607,500 B2 * | 8/2003 | Da Silva | .............. | A61N 1/0472 |
| | | | | 206/438 |
| 2009/0149891 A1 | 6/2009 | Lee et al. | | |
| 2014/0343471 A1 | 11/2014 | Barberio | | |

* cited by examiner

CAST PORTAL

FIELD OF THE INVENTION

The present disclosure relates generally to medical equipment. More specifically, but not by way of limitation, the present disclosure relates to a portal for a medical cast.

BACKGROUND

Medical casts can be used to heal injuries to body parts. A medical cast can be formed around an injured body part by wrapping a cast material, such as plaster or fiberglass, around the body part and allowing the cast material to harden. The hardened cast-material can protect and stabilize the injured body part until the body part is healed. But medical casts are often uncomfortable and block access to the body part(s) covered by the cast. For example, a medical cast that is wrapped around a foot to fix a broken heel may block access to the heel as well as other areas of the foot, such as the toes. This may prevent a user from being able to, for example, scratch, move, or apply medicine to the heel, the toes, or both. What is needed is a way to provide access to areas of a body part covered by a cast.

Also, to heal some injuries, a medical pin may be partially inserted into a body part through an opening in a medical cast, so that a portion of the medical pin protrudes outwardly from the body part and the medical cast. This portion may catch on various articles (e.g., bedding, blanketing, or clothing) or hit various surfaces (e.g., doors, chairs, or tables) creating a significant amount of pain. What is needed is a way to protect such medical pins from contacting various articles and surfaces.

SUMMARY

Some embodiments of the present disclosure may include a device for enabling selective access through a medical cast to a body part covered by the medical cast. The device may comprise an interior portion that extends through an entire longitudinal length of the device. The device may comprise an outer housing that defines the bounds of the interior portion. The outer housing may comprise a top end configured to be positioned distal to the body part covered by the medical cast and a bottom end configured to be positioned proximate to the body part covered by the medical cast. The device may comprise a protrusion extending radially outwardly from the outer housing and configured to mechanically couple with the medical cast for attaching the device to the medical cast.

Other embodiments of the present disclosure may include a system that comprises a medical cast configured to cover a body part. The medical cast may comprise an interior side configured to contact the body part. The medical cast may comprise an exterior side that is opposite to the interior side. The system may comprise an access device that is installable in the medical cast and configured to enable selective access through the medical cast to the body part. The access device may comprise an interior portion that extends through an entire longitudinal length of the access device. The access device may comprise an outer housing that defines the bounds of the interior portion. The outer housing may comprise a top end configured to be positioned distal to the body part covered by the medical cast and extend outwardly from the exterior side of the medical cast. The outer housing may comprise a bottom end configured to be positioned proximate to the body part covered by the medical cast. The system may comprise a coupling device configured to mechanically couple with the medical cast for attaching the access device to the medical cast.

Still other embodiments of the present disclosure may include a method for enabling selective access through a medical cast to a body part covered by the medical cast. The method may comprise obtaining an access device. The access device may comprise an outer housing that defines an interior portion extending through an entire longitudinal length of the access device. The access device may comprise a protrusion extending radially outwardly from the outer housing. The method may comprise positioning a bottom end of the outer housing of the access device proximate to the body part. The method may comprise forming a portion of the medical cast around the protrusion of the access device to secure the access device in position. The method may comprise attaching a cap to a top end of the outer housing of the access device such that the cap encloses another end of the interior portion of the access device.

These illustrative embodiments are mentioned not to limit or define the limits of the present subject matter, but to provide examples to aid understanding thereof. Illustrative embodiments are discussed in the Detailed Description, and further description is provided there. Advantages offered by various embodiments may be further understood by examining this specification and/or by practicing one or more embodiments of the claimed subject matter.

BRIEF DESCRIPTION OF THE FIGURES

A full and enabling disclosure is set forth more particularly in the remainder of the specification. The specification makes reference to the following appended figures.

DETAILED DESCRIPTION

The following description recites various aspects and embodiments of the present invention. No particular embodiment is intended to define the scope of the invention. Rather, the embodiments merely provide non-limiting examples of various methods, systems, and apparatuses that are at least included within the scope of the invention. The description is to be read from the perspective of one of ordinary skill in the art; therefore, information well-known to the skilled artisan may not necessarily be included.

Definitions and Abbreviations

The following terms, unless otherwise indicated, shall be understood to have the following meanings:

As used herein, the terms "a," "an," and "the" can refer to one or more unless specifically noted otherwise.

The term "or" is not to be construed as identifying mutually exclusive options. For example, the phrase "X contains A or B" can mean that X contains A and not B, X contains B and not A, or X contains both A and B. That is, the term "or" is used to mean "and/or" unless explicitly indicated to refer to alternatives only or the alternatives are mutually exclusive, although the disclosure may support a definition that refers to only alternatives and "and/or." As used herein "another" can mean at least a second or more.

Illustrative Embodiments of a Cast Portal

Figure 1:
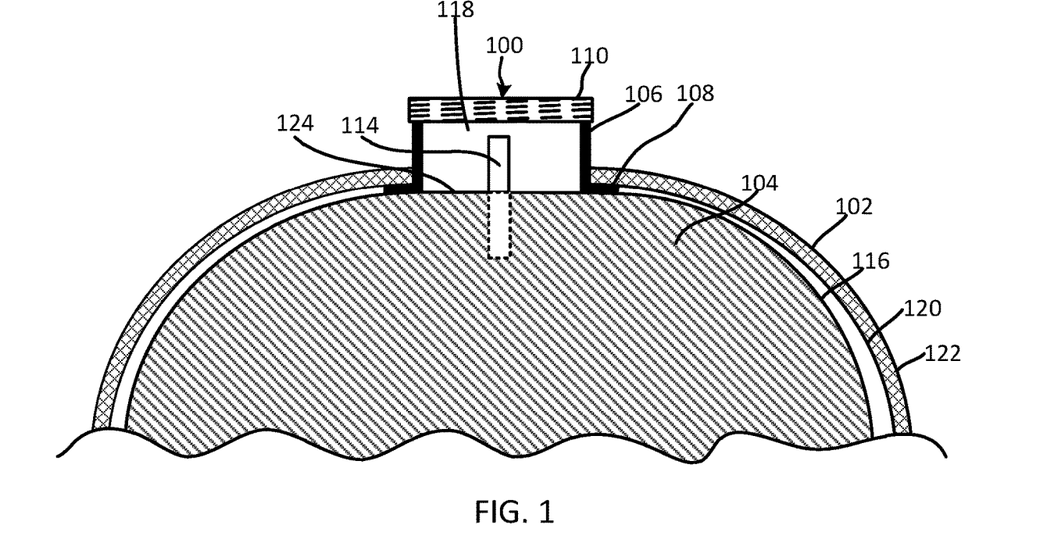
FIG. 1 shows a cross-sectional side view of an embodiment of a cast portal coupled to a medical cast that is covering a body part.

FIG. 1 shows a cross-sectional side view of an embodiment of a cast portal 100 attached to a medical cast 102 that is covering a body part 104, such as a foot, leg, hand, finger, arm, toe, back, chest, or any other body part or combination of body parts. The cast portal 100 can enable a user (e.g., the wearer of the medical cast 102 or another party, such as medical personnel) to selectively access at least a portion of the body part 104 covered by the medical cast 102. The cast portal 100 can additionally or alternatively protect one or more medical components, such as medical component 114, that are at least partially protruding through the medical cast 102. Examples of the medical component 114 may comprise a pin, such as a bone pin; a clamp; a rod; a medical tool; stitches; an adhesive or other material; or any other medical component or combination of medical components.

The cast portal 100 may comprise an outer housing 106. The outer housing 106 may comprise one or more hard materials, soft materials, protective materials, waterproof materials, bacteria-resistant materials, antiseptic materials, deformable materials, flexible materials, or other materials. Examples of the materials may comprise plastic, rubber, fiberglass, metal, wire mesh, or any combination of these. The outer housing 106 may comprise a circular, oval, triangular, rectangular, or any other suitable cross-sectional end shape.

The outer housing 106 can define the bounds of an interior portion 118 of the cast portal 100. In some embodiments, the interior portion 118 of the cast portal 100 is substantially empty (e.g., hollow). For example, the interior portion 118 of the cast portal 100 may be empty. In one embodiment, the interior portion 118 of the cast portal 100 may comprise the medical component 114. Additionally or alternatively, the interior portion 118 may comprise one or more materials, such as any material or materials discussed above.

The cast portal 100 includes a cap 110 that is coupleable to a top end of the outer housing 106. In some embodiments, the cap 110 is removable. For example, the cap 110 may be able to screw on and off of, snap on and off of, or otherwise couple and decouple from the top end of the outer housing 106. As a particular example, the cap 110 may be able to screw on and off of the top end of the outer housing 106 via threads 112 at the top end of the outer housing 106. The cap 110 can be removed to provide access to the portion 124 of the body part 104 covered by the cast portal 100 and/or the medical component 114. For example, the cap 110 can be removed to provide access to stiches or an injury (e.g., a cut or bruise) in the body part 104. And the cap 110 can be attached to block access to the portion 124 of the body part 104 covered by the cast portal 100 and/or the optional medical component 114. For example, the cap 110 can be attached to block dirt, fibers, bacteria, and other debris from contacting the portion 124 of the body part 104 covered by the cast portal 100. In other embodiments, the cap 110 may be permanently fixed to the top end of the outer housing 106.

The cast portal 100 is attachable to the medical cast 102, the body part 104, or both of these. For example, the cast portal 100 can include a coupling device 108 configured to mechanically couple the cast portal 100 to the medical cast 102, the body part 104, or both. Examples of the coupling device 108 can include one or more protrusions, adhesive materials, ridges, channels, clips, pins, hook-and-loop fasteners, screws, bolts, a skirt (e.g., made of nylon or casting tape), or any combination of these. The coupling device 108 can attach the cast portal 100 to an interior side 120 of the medical cast 102, an exterior side 122 of the medical cast, or another layer of the medical cast 102. For example, in the embodiment shown in FIG. 1, the coupling device 108 comprises a protrusion extending outwardly from the outer housing 106 and coupled to an interior side 120 of the medical cast 102. In other embodiments, the protrusion can be integrated in-between one or more layers of material forming the medical cast 102, coupled to an exterior side 122 of the medical cast 102, or any combination of these. For example, the protrusion can be woven or laminated between one or more layers of material forming the medical cast 102.

Figure 2:
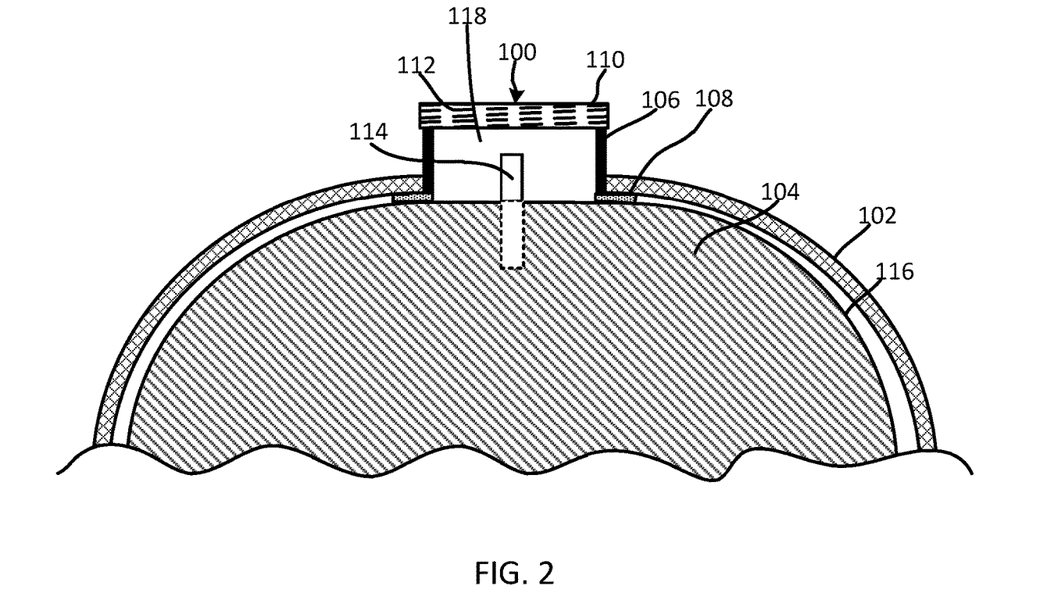
FIG. 2 shows cross-sectional side view of another embodiment of a cast portal coupled to a medical cast that is covering a body part.

Another example of an embodiment of a cast portal 100 is shown in FIG. 2. In the embodiment shown in FIG. 2, the coupling device 108 comprises a deformable material. Examples of the deformable material may comprise rubber, latex, wire mesh, sponge, or an elastic material. The deformable material can flex, bend, or conform to the surface 116 of the body part 104. This may provide enhanced comfort for a user.

Figure 3:
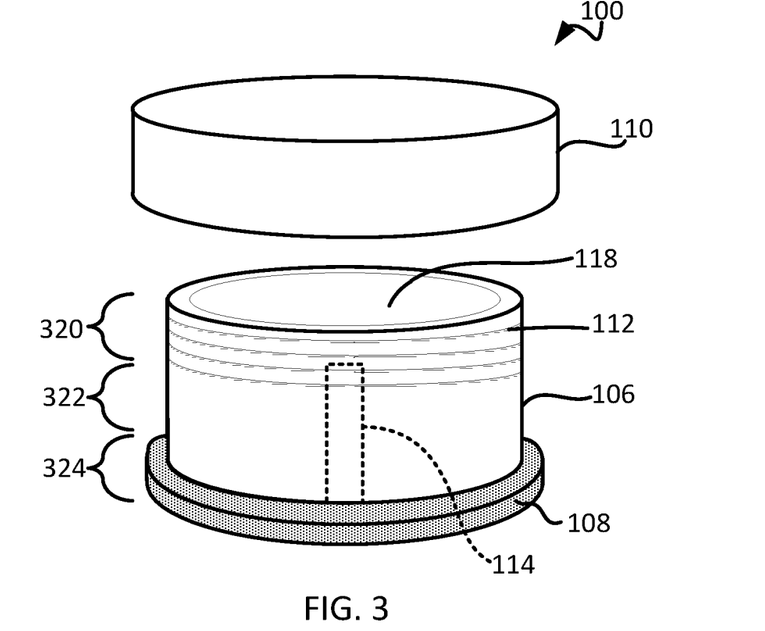
FIG. 3 shows a perspective view of an embodiment of the cast portal shown in FIG. 2.

FIG. 3 shows a perspective view of an embodiment of the cast portal 100 shown in FIG. 2. The outer housing 106 of the cast portal 100 has a top end 320, a middle portion 322, and a bottom end 324. The top end 320 may comprise one or more threads 112 for enabling the cap 110 to screw on and off of the top end 320. The top end 320 can be configured to be positioned distal to a body part 104 covered by a medical cast 102. The bottom end 324 may be configured to contact a body part or be positioned proximate to (e.g., near to, such as within 1 inch) the body part 104. In the embodiment shown in FIG. 3, the coupling device 108 comprises a protrusion that extends radially outwardly from the outer housing 106 and substantially encircles the outer housing

106. In some embodiments, the protrusion can extend 2 inches or more outwardly from the outer housing 106.

Figure 4:
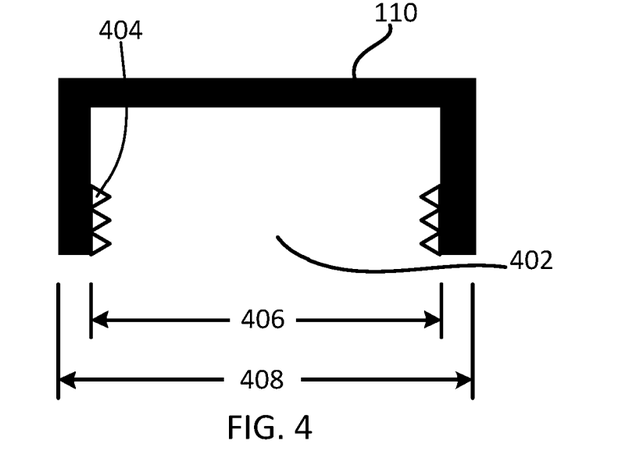
FIG. 4 shows a cross-sectional side view of the cap for the cast portal shown in FIG. 3.

FIG. 4 shows a cross-sectional side view of a cap 110 for a cast portal 100. In the embodiments shown in FIG. 4, the cap 110 includes one or more ridges 404 for enabling the cap 110 to screw onto threads 112 at the top end 320 of the outer housing 106 of the cast portal 100. Additionally or alternatively, the cap 110 can include other coupling devices for enabling the cap 110 to couple with the top end 320 of the outer housing 106.

In some embodiments, the cap 110 has an inner diameter 406 that is larger than an outer diameter of the top end 320 of the outer housing 106. This can enable an interior 402 of the cap 110 to receive and at least partially enclose the top end 320 of the outer housing 106. In one such embodiment, the cap 110 and the top end 320 of the outer housing 106 can be dimensioned so as to enable the cap 110 to frictionally couple with (e.g., fit snugly around) the top end 320 of the outer housing 106 for securing the cap 110 to the cast portal 100.

In other embodiments, the outer diameter 408 of the cap 110 can be smaller than an inner diameter of the interior 118 of the cast portal 100. This can enable the interior 118 of the cast portal 100 to receive and at least partially enclose the cap 110. In one such embodiment, the cap 110 and the interior 118 of the cast portal 100 can be dimensioned so as to enable the cap 110 to fit snugly within the interior 118 of the cast portal 100 for securing the cap 110 to the cast portal 100.

Figure 5:
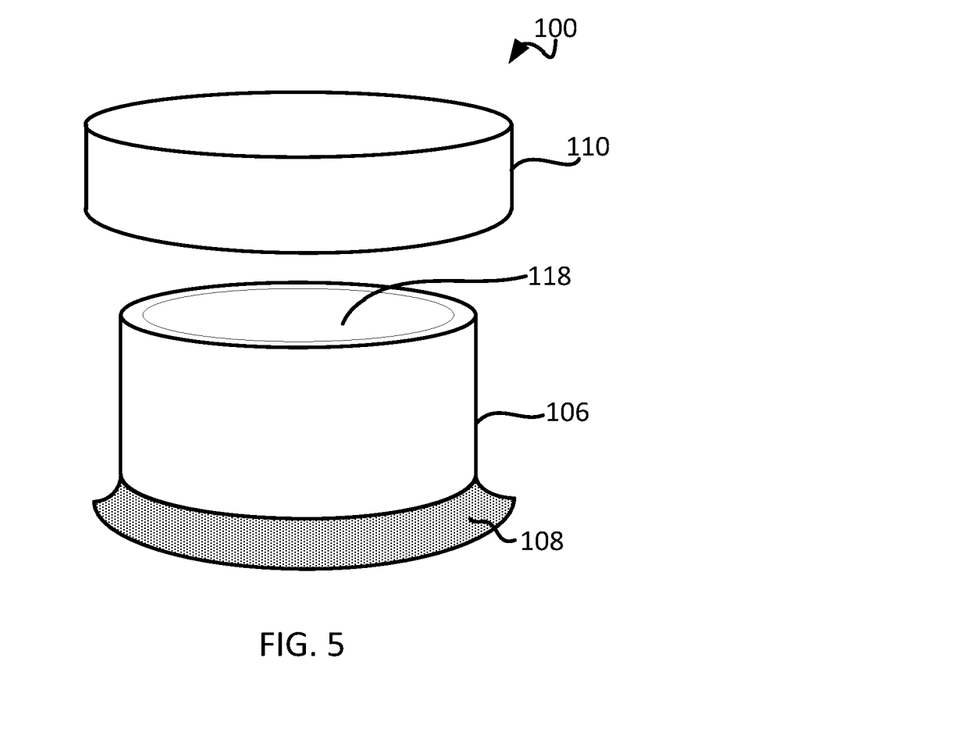
FIG. 5 shows a perspective view of another embodiment of the cast portal shown in FIG. 2.

FIG. 5 shows a perspective view of another embodiment of the cast portal 100 shown in FIG. 2. In the embodiment shown in FIG. 5, the coupling device 108 comprises a skirt or a curved protrusion. The curvature may enable the coupling device 108 to conform to the surface 116 of the body part 104 more easily and provide enhanced comfort. Additionally or alternatively, the curvature may enable the coupling device 108 to be more easily woven or positioned between layers of a medical cast 102.

Although the coupling devices 108 of FIGS. 3 and 5 are shown as having a circular shape that encircles the outer housing 106, in other embodiments, the coupling device 108 may comprise another shape, such as a square shape, rectangular shape, triangular shape, etc. Further, although the coupling device 108 is shown as a substantially continuous piece of material, in other embodiments, the coupling device 108 may comprise two or more separate pieces of material spaced apart around the bottom of the outer housing 106 (or elsewhere on the outer housing 106).

Figure 6:
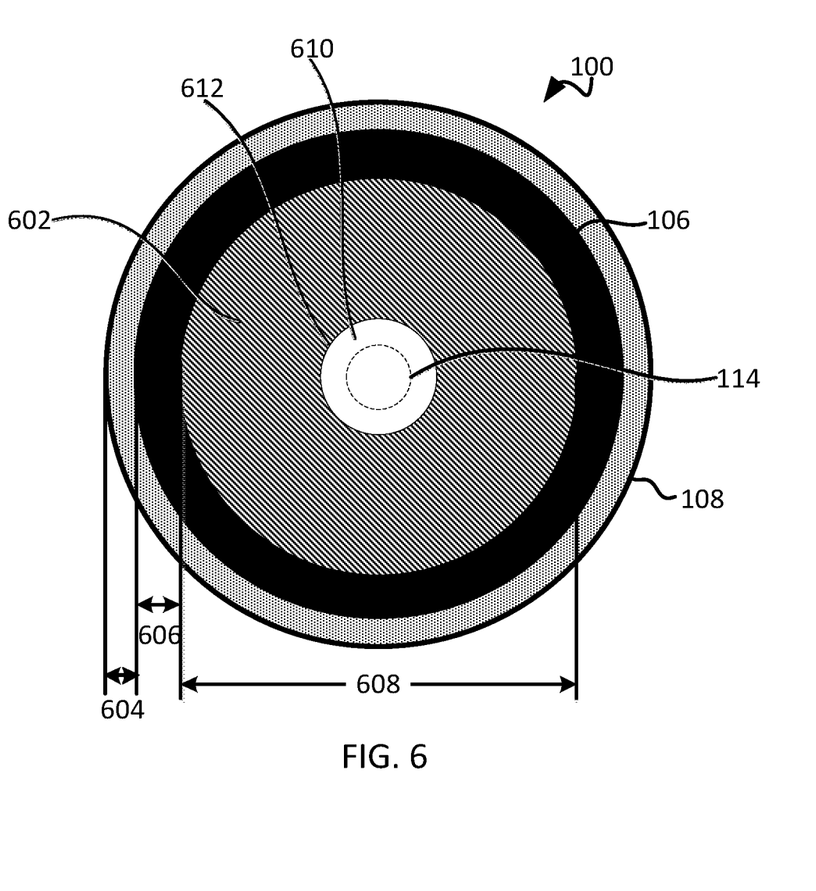
FIG. 6 shows a cross-sectional end view of an embodiment of a cast portal.

Turning now to FIG. 6, FIG. 6 shows a cross-sectional end view of an embodiment of the cast portal 100. The outer housing 106 of the cast portal 100 can have any suitable wall thickness 606. In some embodiments, the wall thickness 606 is between 1 millimeter (mm) and 7 mm.

The cast portal 100 may also comprise a coupling device 108, such as a protrusion, that extends outwardly from the outer housing 106 by length 604. In some embodiments, length 604 is between 12 mm and 100 mm.

The cast portal 100 can also have an inner diameter 608 of any suitable size, such as between 15 mm and 100 mm. In some embodiments, the inner diameter 608 may be large enough to enable the medical component 114 to fit and move around within the inner diameter 608 of the cast portal 100. This may allow for the natural movement of the medical component 114 as the user moves the body part covered by the cast portal 100, without the medical component 114 hitting an inner wall of the outer housing 106 of the cast portal 100.

In some embodiments, the cast portal 100 comprises one or more materials 602 within the inner diameter 608. The material(s) 602 may stabilize the medical component 114, prevent infection, or prevent debris from entering through the cast portal 100. The material(s) 602 can include hard materials, soft materials, protective materials, waterproof materials, bacteria-resistant materials, antiseptic materials, deformable materials, sponge materials, or any combination of these. The material(s) 602 may comprise circular, oval, square, triangular, donut, or any other suitable cross-sectional end shape. The material(s) 602 can be removable or permanently positioned within the cast portal 100. For example, the material(s) 602 can be positioned within, and removable from, the cast portal 100. A user can remove the cap 110 from the cast portal 100 and remove the material(s) 602, as desired (e.g., to access the portion 124 of the body part 104 covered by the cast portal 100). The user can then insert the material(s) 602 back inside the cast portal 100 and reattach the cap 110.

In some embodiments, a hole 610 is formed through the material(s) 602. The hole 610 may enable the medical component 114 to fit through the material(s) 602 or to enable air to flow through the material(s) 602. The hole 610 may comprise circular, oval, square, triangular, donut, or any other suitable cross-sectional end shape. In some embodiments, hole 610 is large enough to enable the medical component 114 to fit and move around within the hole 610. This may allow for the natural movement of the medical component 114 as the user moves the body part covered by the cast portal 100, without the medical component 114 hitting an inner wall 612 of the material(s) 602 forming the hole 610. Although only one hole 610 is shown in FIG. 6, any number of holes, having any combination of shapes and sizes, can be formed through the material(s) 602.

Figure 7:
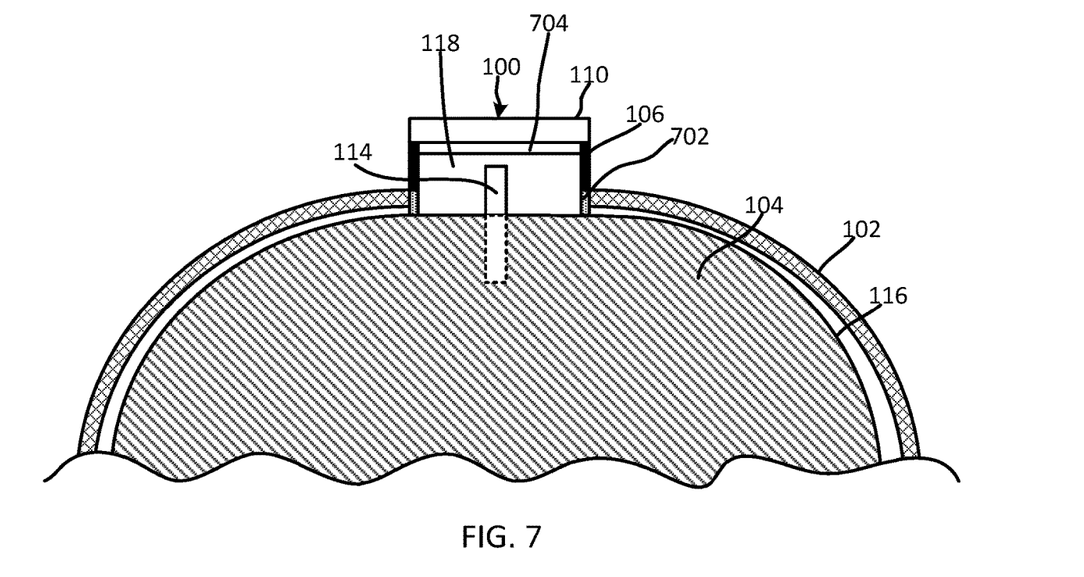
FIG. 7 shows cross-sectional side view of another embodiment of a cast portal coupled to a medical cast that is covering a body part.

FIG. 7 shows cross-sectional side view of another embodiment of the cast portal 100 coupled to the medical cast 102 that is covering the body part 104. In the embodiment shown in FIG. 7, a bottom end of the outer housing 106 comprises a layer of material 702. The layer of material 702 may comprise a deformable material or another material for enhancing the comfort of the cast portal 100. Additionally or alternatively, the material 702 can enable or improve a coupling between the cast portal 100 and the medical cast 102.

In the embodiment shown in FIG. 7, the cap 110 of the cast portal 100 comprises a plug 704 or stopper configured to fit snugly within the inner diameter of the outer housing 106 of the cast portal 100. This may help couple the cap 110 to the cast portal 100.

Figure 8:
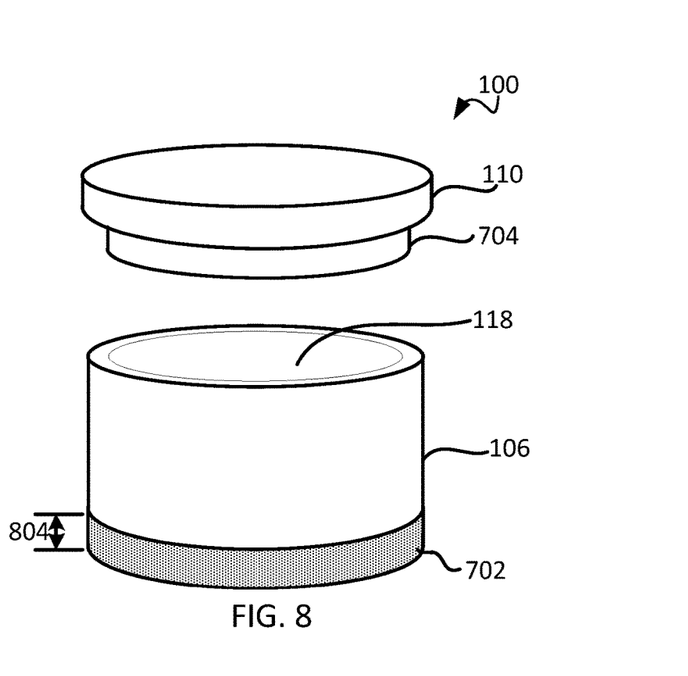
FIG. 8 shows a perspective view of the embodiment of the cast portal shown in FIG. 7.

FIG. 8 shows a perspective view of the embodiment of the cast portal 100 shown in FIG. 7. In the embodiment shown in FIG. 8, the outer housing 106 comprises or is coupled to the layer of material 702. The layer of material 702 may be deformable to enable the layer of material 702 to (i) conform to the surface 116 of the body part 104 more easily and provide enhanced comfort, and/or (ii) be woven or otherwise positioned between layers of the medical cast 102 for securing the cast portal 100 to the medical cast 102. The layer of material 702 can have any suitable longitudinal length 804, such as 6 mm.

Although the layer of material 702 is shown as having a circular shape that corresponds to the circular shape of the outer housing 106, in other embodiments, the layer of material 702 may comprise another shape. Further, although the layer of material 702 is shown as a substantially continuous piece of material, in other embodiments, the layer of material 702 may comprise two or more separate pieces of material spaced apart at the bottom of the outer housing 106 (or elsewhere on the outer housing 106).

Various embodiments have been described above for illustrative purposes. But the present disclosure is not limited to such embodiments, and various features of the abovementioned embodiments can be removed, combined, repositioned, or replaced.

Figure 9:
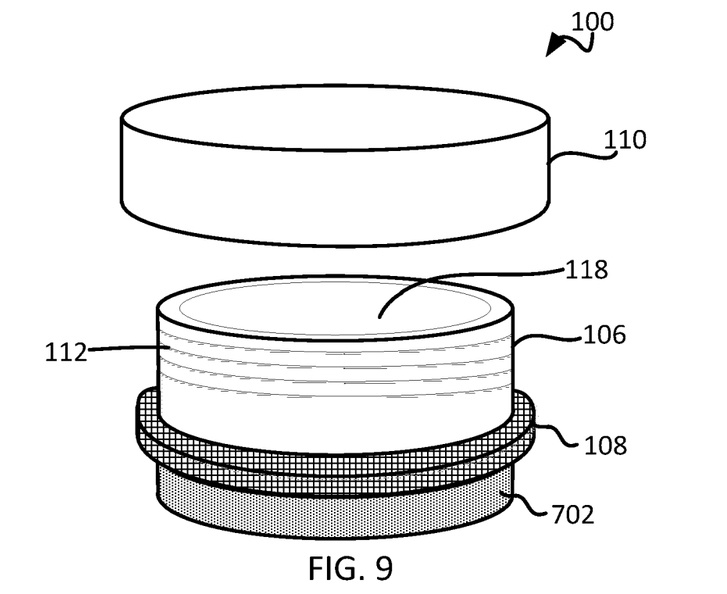
FIG. 9 shows a perspective view of another embodiment of a cast portal.

For example, FIG. 9 shows a perspective view of another embodiment of the cast portal 100. In this embodiment, the top end of the outer housing 106 has threads for removably coupling with the cap 110. Also, the coupling device 108 is positioned at the middle portion of the outer housing 106. Further, the layer of material 702 is positioned at the bottom end of the outer housing 106.

Figure 10:
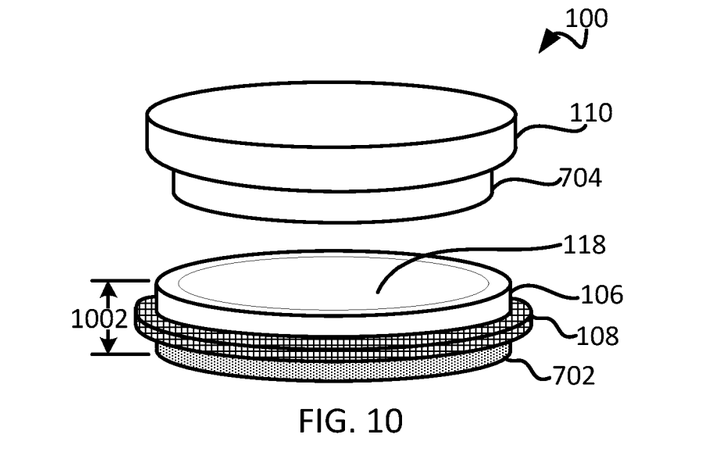
FIG. 10 shows a perspective view of still another embodiment of a cast portal.

FIG. 10 shows a perspective view of still another embodiment of the cast portal 100. In this embodiment, the top end of the outer housing 106 does not have threads. Instead, the cap 110 has the plug 704 for frictionally coupling with the inner wall of the outer housing 106. Also, in this embodiment, the coupling device 108 is positioned at the middle portion of the outer housing 106. Further, in this embodiment, the longitudinal length 1002 of the outer housing 106 is shorter than in other embodiments. But the longitudinal length 1002 of the outer housing 106 can be any suitable length, such as between 6 mm and 51 mm.

Figure 11:
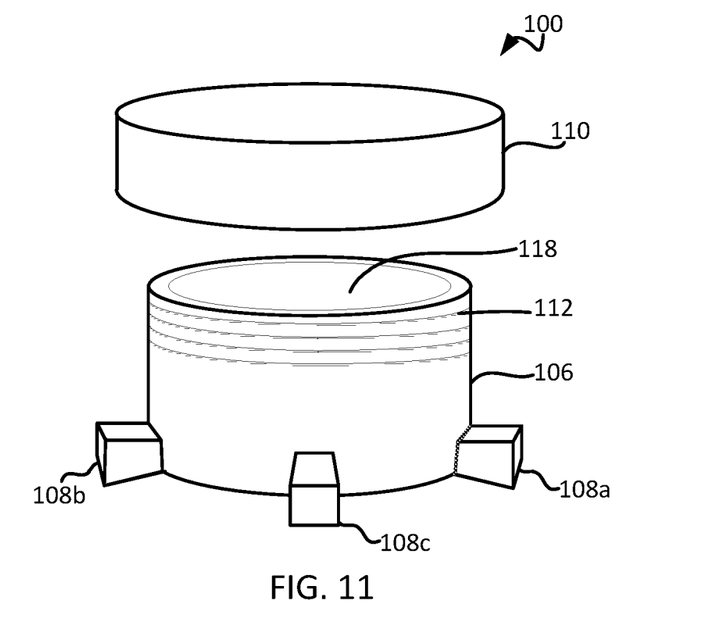
FIG. 11 shows a perspective view of yet another embodiment of a cast portal.

FIG. 11 shows a perspective view of yet another embodiment of the cast portal 100. In the embodiment shown in FIG. 11, the outer housing 106 comprises threads 112 for enabling the cap 110 to screw onto the outer housing 106. The embodiment shown in FIG. 11 also comprises multiple coupling devices 108*a-c* (e.g., protrusions) extending outwardly from the bottom end of the outer housing 106. The coupling devices 108*a-c* can be positioned at regular or irregular intervals around the bottom end of the outer housing 106. The coupling devices 108*a-c* may comprise any number and combination of materials, such as deformable materials for comfort and adhesive materials for enhanced coupling with a medical cast 102.

Figure 12:
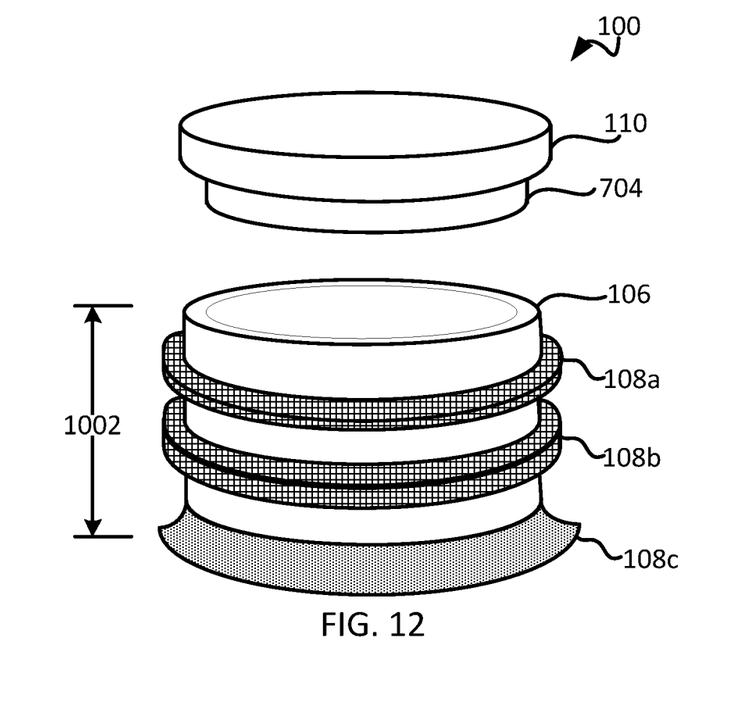
FIG. 12 shows a perspective view of another embodiment of a cast portal.

Although FIG. 11 depicts three protrusions positioned around the bottom end of the outer housing 106, the cast portal 100 may comprise any number of coupling devices 108*a-c*, having any combination of shapes, types, sizes, and materials, at any number and combination of locations on the outer housing 106. For example, as shown in FIG. 12, the cast portal 100 may comprise multiple coupling devices 108*a-c* positioned along the longitudinal length 1002 of the outer housing 106. The coupling devices 108*a-c* can be protrusions having different lengths and shapes. In alternative embodiments, the coupling devices 108*a-c* can be of different types. For example, the coupling device 108*a* may be a clip configured to attach to an upper layer of the cast material used to form the medical cast 102. The coupling device 108*b* may be a protrusion configured to integrate with a middle layer of the cast material used to form the medical cast 102. The coupling device 108*c* may be an adhesive configured to be positioned underneath a bottom layer of the cast material used to form the medical cast 102. The use of multiple coupling devices 108*a-c* may more securely hold the cast portal 100 in place.

Figure 13A:
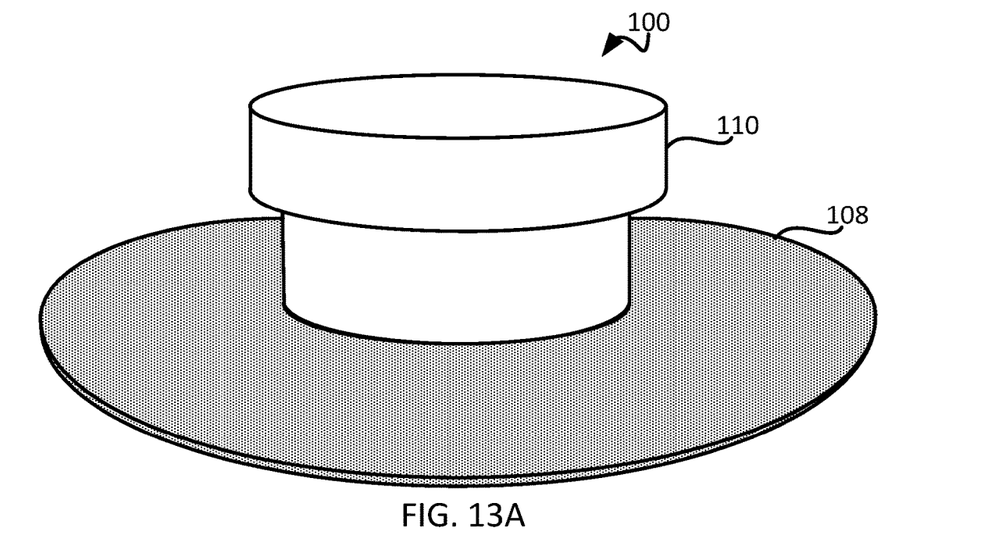
FIG. 13A shows a perspective view of another embodiment of a cast portal.

FIG. 13A shows a perspective view of another embodiment of a cast portal 100. In this example, the cap 110 is attached to the cast portal 108. The cast portal 108 includes a coupling device 108 that can be, for example, casting tape, nylon, or a fiberglass mesh. The coupling device 108 may have a disk shape. The coupling device 108 can be laminated between layers of the medical cast 102 to secure the cast portal 100 to the medical cast 102. For example, the coupling device 108 can extend several inches (e.g., two inches) radially outwardly from the outer housing 106 of the cast portal 100. The coupling device 108 can be wrapped between the layers of the medical cast 102 as the medical cast 102 is being applied to a body part 104. Heat or pressure can then be applied to the layers of the medical cast 102 to secure the layers of the medical cast 102, along with the coupling device 108, in place.

Figure 13B:
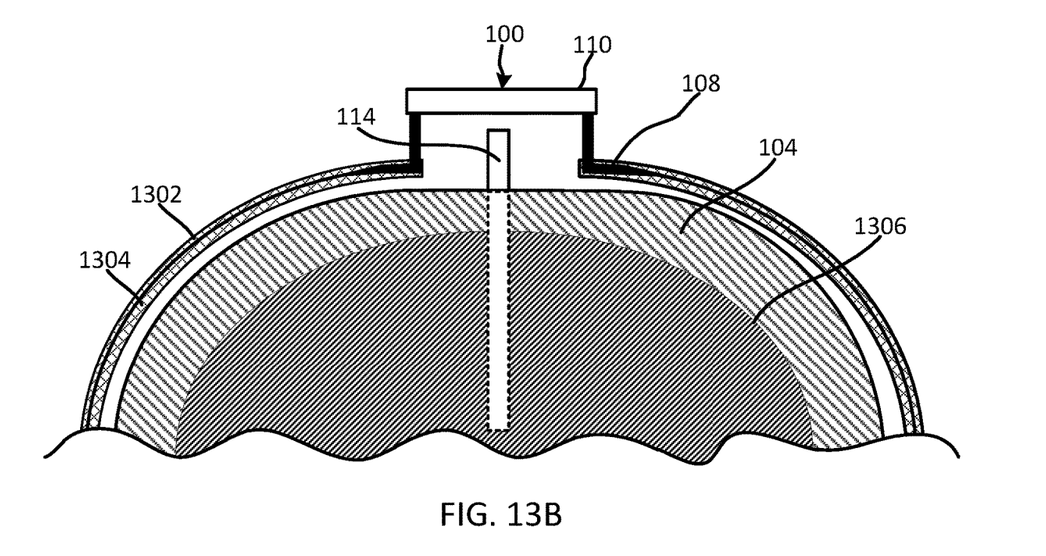
FIG. 13B shows a cross-sectional side view of the cast portal of FIG. 13A coupled to a medical cast that is covering a body part.

FIG. 13B shows a cross-sectional side view of the cast portal 100 of FIG. 13A coupled to a medical cast 102 that is covering a body part 104. As discussed above, in some examples, a medical component 114 can extend into the body part 104 (and into bone 1306, a joint, a ligament, a muscle, etc.).

As shown in FIG. 13B, the coupling device 108 of the cast portal 100 is at least partially integrated between layers of the medical cast 102. For example, the coupling device 108 can include a protrusion (e.g., formed from casting tape, or a nylon or fiberglass mesh) integrated between the layers 1302-1304 of the medical cast 102. Thus, the cast portal 100 may not contact the body part 104. This may prevent the cast portal 100 from rubbing against or otherwise aggravating the body part 104 (or skin near the body part 104).

In some embodiments, the coupling device 108 of the cast portal 100 can be laminated between the layers 1302-1304 of the medical cast 102 as the layers 1302-1304 are being wrapped around the body part 104. This may secure the cast portal 100 to the medical cast 102.

Figure 14:
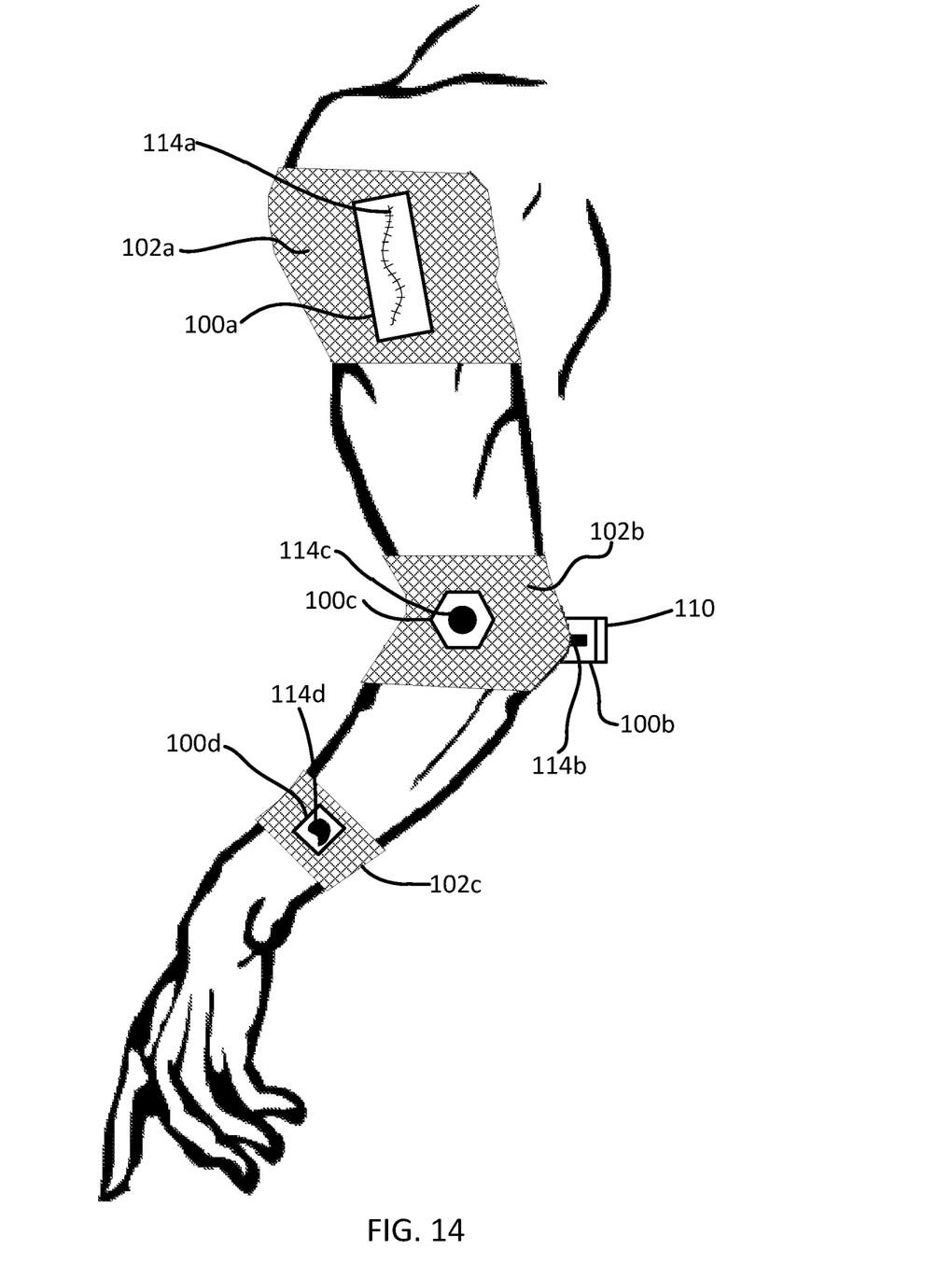
FIG. 14 shows a perspective view of multiple cast portals coupled to multiple medical casts covering multiple body parts.

FIG. 14 shows a perspective view of multiple cast portals 100*a-d* coupled to multiple medical casts 102*a-c* covering multiple body parts. In the embodiment shown in FIG. 14, cast portal 100*a* is coupled to medical cast 102*a* covering a shoulder. The cast portal 100*a* is transparent, enabling the medical component 114*a* (in this example, stitches) to be visible through the cast portal 100*a*. Another cast portal 100*b* is coupled to another medical cast 102*b* covering an elbow. The cast portal 100*b* is also transparent, enabling the medical component 114*b* (in this example, a pin) to be visible through the cast portal 100*b*. Cast portal 100*c* is also coupled to the medical cast 102*b* and is also transparent, enabling the medical component 114*c* (in this example, a thicker pin) to be visible through the cast portal 100*c*. Still another cast portal 100*d* is coupled to another medical cast 102*c* covering a forearm or wrist. The cast portal 100*d* is also transparent, enabling the medical component 114*d* (in this example, a material for aiding the healing of a wound) to be visible through the cast portal 100*d*. In other embodiments, one or more of the cast portals 100*a-d* may not be transparent.

As shown in FIG. 14, the cast portals 100*a-d* can be different shapes and sizes. For example, cast portal 100*a* has a rectangular shape, cast portal 100*b* has a cylindrical shape, cast portal 100*c* has a hexagonal shape, and cast portal 100*d* has a square shape. In other embodiments, the cast portals 100*a-d* can include other shapes, such as triangular, star, oval, trapezoidal, and octagonal shapes. The cast portals 100*a-d* can have any number and combination of shapes and sizes.

Any number and configuration of cast portals 100*a-d* can be coupled to any number any configuration of medical casts 102*a-c* covering any number and configuration of body parts. For example, as shown in FIG. 14, two cast portals 100*b-c* can be coupled to a single medical cast 102*b*. In other embodiments, all of the cast portals 100*a-d* can be coupled to a single, continuous medical cast.

Illustrative Methods for Using a Cast Portal

Figure 15:
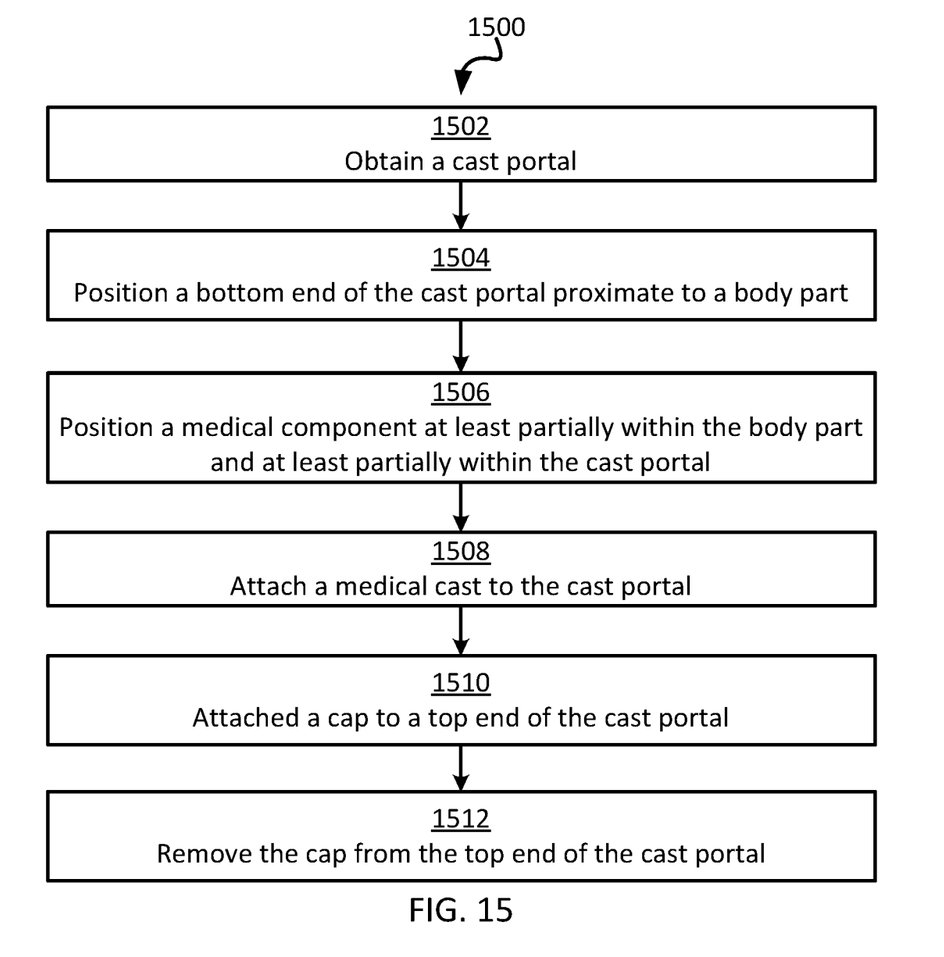
FIG. 15 shows an example of a flow chart of steps for performing a method for attaching a cast portal to a medical cast.

FIG. 15 shows an example of a flow chart of steps for performing a method 1500 for attaching a cast portal 100 to a medical cast 102. Some embodiments may include more, fewer, or different steps, which may be in the same order or in a different order. For example, some embodiments may exclude step 1506. The steps below are described with reference to components shown in FIGS. 1-13.

In some embodiments, the method 1500 comprises obtaining a cast portal 100, as shown in block 1502. For example, the cast portal 100 can be obtained from a manufacturer, distributer, hospital, doctor, or another entity.

In some embodiments, the cast portal 100 can be formed or obtained using a three-dimensional (3D) printer, injection molding, or another manufacturing process. For example, a user can input the characteristics of the cast portal 100 into a 3D printer and print his or her own cast portal 100 at his or her own house.

In some embodiments, the cast portal 100 can be specifically designed to account for one or more physical characteristics of the body part (e.g., the contour, hairiness, color, size, shape, etc.) over which the cast portal 100 will lie. For example, if the cast portal 100 is to be applied to a user's arm, a manufacturer of the cast portal 100 can input into a computing device one or more physical characteristics (e.g., dimensions, curvatures, divots, bulges, etc.) of the user's arm. Alternatively, a 2D or 3D scan of the user's arm can be taken using a scanning device (e.g., one or more cameras, depth sensors, ultrasonic transducers, etc.), and the scanning device can provide information associated with the physical characteristics of the user's arm to the computing device. The computing device can then adjust at least a portion of a CAD model, schematic, or rendering of the cast portal 100 to account for the physical characteristics of the user's arm. For example, the computing device can automatically adjust the dimensions of the bottom end 324 of the cast portal 100 in a CAD model of the cast portal 100 to account for a curvature in the user's arm. The cast portal 100 can then be produced according to the updated CAD model of the cast portal 100. For example, the cast portal 100 can be printed using a 3D printer using the updated CAD model.

In some embodiments, the method 1500 comprises positioning a bottom end 324 of the cast portal 100 proximate to a body part 104, as shown in block 1504. For example, the bottom end 324 can be pressed against or positioned on the body part 104. Alternatively, the bottom end 324 can be positioned above, but not contacting, the body part 104 (e.g., so that there is a space between the bottom end 324 and the body part).

In some cases, a medical procedure may include positioning a medical component 114 into the body part 104 such that the medical component 114 extends outwardly from the body part 104. In such cases, the method 1500 may comprise positioning a medical component 114 at least partially within the body part 104 and at least partially within the cast portal 100, as shown in block 1506. For example, the medical component 114 can be inserted through the interior portion 118 of the cast portal 100 and partially into the body part 104, so that a portion of the medical component 114 extends into the interior portion 118 of the cast portal 100. In alternative embodiments, the medical component 114 can be positioned at least partially within the body part 104 prior to the cast portal 100 being positioned proximate to the body part 104. For example, a medical pin can be positioned partially within the body part 104 and the cast portal 100 can then subsequently be positioned around the medical pin.

In some embodiments, the medical component 114 may not be partially positioned in the body part 104, but rather may be attached to a surface 116 of the body part 104. For example, the medical component 114 may be a bandage, gauze, or other material positioned over a wound in the body part 104. In such an embodiment, the medical component 114 may or may not protrude into the interior portion 118 of the cast portal 100. And the method 1500 may comprise positioning the medical component 114 on the surface 116 of the body part 104 before or after positioning the bottom end 324 of the cast portal 100 proximate to the body part 104.

In some embodiments, the method 1500 comprises attaching a medical cast 102 to the cast portal 100 (or attaching the cast portal 100 to the medical cast 102), as shown in block 1508. For example, the cast portal 100 can be positioned against a body part 104 and have a coupling device 108 comprising one or more protrusions. The cast material for the medical cast 102 can be wrapped around the body part 104 and at least partially overtop of the protrusion(s). This process may be repeated multiple times so that the cast material overlaps the protrusion(s) with multiple layers (and/or at multiple angles) to further secure the cast portal 100 to the body part 104. Once the cast material hardens, the rigidity of the cast material may keep the cast portal 100 in place.

As another example, the cast portal 100 may be clipped, screwed, bolted, glued, adhered, or otherwise attached to the medical cast 102 via the coupling device 108. For instance, a hole can be cut through a medical cast 102 that has been formed around the body part 104. The cast portal 100 can be inserted through the hole in the medical cast 102 so that the bottom end 324 of the cast portal 100 is proximate to the body part 104. The cast portal 100 can then be secured in place via the coupling device 108. For example, the cast portal 100 can be glued, screwed, or clipped to medical cast 102 to secure the cast portal 100 in position.

In some embodiments, the method 1500 comprises attaching a cap 110 to a top end 320 of the cast portal 100, as shown in block 1510. For example, the cap 110 can be screwed, glued, clipped, press-fitted, snapped, pushed, or otherwise manipulated into position at the top end 320 of the cast portal 100.

In some embodiments, the method 1500 comprises removing the cap 110 from the top end 320 of the cast portal 100, as shown in block 1512. For example, the cap 110 can be unscrewed, unclipped, unsnapped, pulled, or otherwise manipulated to remove the cap 110 from the top end 320 of the cast portal 100.

Although the above steps are described for illustrative purposes, other embodiments can include the same or different steps performed in the same or different order. For example, in another embodiment, a cast portal 100 can be formed into, or otherwise integrated with, a medical cast 102 as the medical cast 102 is being applied to a body part 104. For example, as the layers of material forming the medical cast 102 are being wrapped around the body part 104, the coupling device 108 (e.g., a flexible material made of cast tape, nylon, and/or fiberglass) of the cast portal 100 can be integrated between the layers of material, so that when the layers of material harden, the cast portal 100 is secured in position. In such an embodiment, the bottom end 324 of the cast portal 100 may not contact the user's skin.

Advantages of Embodiments

Embodiments of the present disclosure provide numerous advantages. For example, some embodiments can enable a user (e.g., a patient or medical personnel) to access a body part covered by a cast to, for example, monitor, scratch, itch, move, or apply medicine to the body part. Some embodiments may additionally or alternatively cover an opening in a medical cast to prevent dirt, hair, or other debris from contacting, damaging, causing an infection in, or otherwise affecting an injured portion of the body. Further, some embodiments may surround and protect a medical component protruding from the user's body to prevent the medical component from catching on or contacting various articles and surfaces, minimizing or eliminating pain associated therewith.

Example Embodiments

In some embodiments, a device of the present disclosure is usable for enabling selective access through a medical cast to a body part covered by the medical cast and comprises: an interior portion that extends through an entire longitudinal length of the device; an outer housing that defines the bounds of the interior portion and includes: a top end configured to be positioned distal to the body part covered by the medical cast, and a bottom end configured to be positioned proximate to the body part covered by the medical cast; and a protrusion extending radially outwardly from the outer housing and configured to mechanically couple with the medical cast for attaching the device to the medical cast. In some embodiments, the top end of the outer housing is configured to removably couple with a cap for selectively enclosing the interior portion of the device, and the top end of the outer housing has a smaller diameter than an internal portion of the cap for enabling the cap to receive the top end of the outer housing of the device. In some embodiments, the top end of the outer housing comprises threads configured to enable the cap to screw onto the device. In some embodiments, the top end of the outer housing is configured to frictionally couple with the interior portion of the cap. In some embodiments, the top end of the outer housing is configured to receive a plug extending outwardly from a cap for enclosing the interior portion of the device. In some embodiments, the interior portion of the outer housing is configured to surround a medical component such that the medical component is positionable and/or movable within the interior portion of the device. In some embodiments, the device includes a deformable material configured to conform to a surface of the body part. In some embodiments, the protrusion is positioned at the bottom end of the outer housing and comprises the deformable material. In some embodiments, the protrusion is positioned at a central portion of the outer housing that is between the top end of the outer housing and the bottom end of the outer housing, and the bottom end of the outer housing comprises the deformable material. In some embodiments, the device includes a cap and the interior portion is empty.

In other embodiments, a system of the present disclosure comprises a medical cast configured to cover a body part. The medical cast comprises an interior side configured to contact the body part, and an exterior side that is opposite to the interior side. The system also comprises an access device that is installable in the medical cast and configured to enable selective access through the medical cast to the body part. The access device comprises an interior portion that extends through an entire longitudinal length of the access device; an outer housing that defines the bounds of the interior portion and includes: a top end configured to be positioned distal to the body part and extend outwardly from the exterior side of the medical cast, and a bottom end configured to be positioned proximate to the body part; and a coupling device configured to mechanically couple with the medical cast for attaching the access device to the medical cast. In some embodiments, the access device is positioned through the medical cast and the top end is configured to removably couple with a cap. In some embodiments, the interior portion of the access device is configured to surround a medical component. In some embodiments, the medical component is positionable and/or moveable within the interior portion of the access device. In some embodiments, the top end of the access device has a smaller diameter than an internal portion of the cap for enabling the cap to receive the top end of the access device. In some embodiments, the coupling device comprises a protrusion extending radially outwardly from the outer housing.

In still other embodiments, a method of the present disclosure can be for enabling selective access through a medical cast to a body part covered by the medical cast and comprise obtaining an access device that includes: an outer housing that defines an interior portion extending through an entire longitudinal length of the access device, and a protrusion extending radially outwardly from the outer housing; positioning a bottom end of the outer housing of the access device proximate to the body part; forming a portion of the medical cast around the protrusion of the access device to secure the access device in position; and attaching a cap to a top end of the outer housing of the access device such that the cap encloses another end of the interior portion of the access device. In some embodiments, the method includes positioning a medical component at least partially within the body part and at least partially within the interior portion of the access device. In some embodiments, the method includes, prior to forming the portion of the medical cast around the protrusion, positioning a material within the interior portion of the access device and around the medical component to keep the medical component substantially centered within the interior portion of the access device. In some embodiments, the method includes, after forming the portion of the medical cast around the protrusion, removing the material from the interior portion of the access device. In some embodiments, the method includes removing the cap from the top end of the outer housing to access the body part through the interior portion of the access device.

What is claimed is:

1. A device for enabling selective access through a medical cast to a body part covered by the medical cast, the device comprising:
   an interior portion that extends through an entire longitudinal length of the device; an outer housing that defines the bounds of the interior portion and includes: a top end configured to be positioned distal to the body part covered by the medical cast; and
   a bottom end configured to be positioned proximate to the body part covered by the medical cast;
       wherein the top end of the outer housing is configured to removably couple with a cap for selectively enclosing the interior portion of the device, and wherein the top end has a smaller diameter than an internal portion of the cap for enabling the cap to receive the top end of the outer housing of the device; and
   a protrusion extending radially outwardly from the outer housing and configured to mechanically couple with the medical cast for attaching the device to the medical cast, wherein the device is configured to account for one or more physical characteristics of the body part, over which the device will lie;
   wherein the interior portion of the outer housing is configured to surround a medical component, such that the medical component is positionable within the interior portion of the device;

wherein the medical component is selected from the group consisting of a pin, a clamp, a rod, a medical tool, stitches, an adhesive, a bandage, and gauze.

2. The device of claim 1, wherein the top end of the outer housing comprises threads configured to enable the cap to screw onto the device.

3. The device of claim 1, wherein the top end of the outer housing is configured to frictionally couple with the interior portion of the cap.

4. The device of claim 1, wherein the top end of the outer housing is configured to receive a plug extending outwardly from a cap for enclosing the interior portion of the device.

5. The device of claim 1, further comprising a deformable material configured to conform to a surface of the body part.

6. The device of claim 5, wherein the protrusion is positioned at the bottom end of the outer housing and comprises the deformable material.

7. The device of claim 5, wherein the protrusion is positioned at a central portion of the outer housing that is between the top end of the outer housing and the bottom end of the outer housing, and wherein the bottom end of the outer housing comprises the deformable material.

8. A method for enabling selective access through a medical cast to a body part covered by the medical cast, the method comprising:
obtaining the device of claim 1;
forming a portion of the medical cast around the protrusion of the device to secure the device in position; and
attaching the cap to the top end of the outer housing of the device.

9. The method of claim 8, further comprising: positioning the medical component at least partially within the body part and at least partially within the interior portion of the access device.

10. The method of claim 9, further comprising:
prior to forming the portion of the medical cast around the protrusion, positioning a material within the interior portion of the access device and around the medical component to keep the medical component substantially centered within the interior portion of the access device; and
after forming the portion of the medical cast around the protrusion, removing the material from the interior portion of the access device.

11. The method of claim 8, further comprising:
removing the cap from the top end of the outer housing to access the body part through the interior portion of the access device.

12. A system comprising:
a medical cast configured to cover a body part, the medical cast comprising:
an interior side configured to contact the body part; and
an exterior side that is opposite to the interior side; and
an access device that is installable in the medical cast, positioned through the medical cast, and configured to enable selective access through the medical cast to the body part, the access device comprising:
an interior portion that extends through an entire longitudinal length of the access device, wherein the interior portion is configured to surround a medical component;
an outer housing that defines the bounds of the interior portion and includes:
a top end configured to be positioned distal to the body part and extend outwardly from the exterior side of the medical cast, wherein the top end is configured to removably couple with a cap, and the top end has a smaller diameter than an internal portion of the cap for enabling the cap to receive the top end of the access device; and
a bottom end configured to be positioned proximate to the body part; and
a coupling device configured to mechanically couple with the medical cast for attaching the access device to the medical cast.

13. The system of claim 12, wherein the medical component is positionable within the interior portion of the access device.

14. The system of claim 12, wherein the coupling device comprises a protrusion extending radially outwardly from the outer housing, wherein the protrusion is integrated in between one or more layer of materials forming the medical cast.

15. The system of claim 12, wherein the interior portion comprises one or more materials within the inner diameter; wherein the one or more materials are formed such that the medical component may fit through the one or more materials.

* * * * *